(12) United States Patent
Kao

(10) Patent No.: US 9,233,014 B2
(45) Date of Patent: *Jan. 12, 2016

(54) STENT WITH SUPPORT BRACES

(75) Inventor: Stephen Kao, Sunnyvale, CA (US)

(73) Assignee: VENITI, INC., Fremont, CA (US)

( * ) Notice: Subject to any disclaimer, the term of this patent is extended or adjusted under 35 U.S.C. 154(b) by 104 days.

This patent is subject to a terminal disclaimer.

(21) Appl. No.: 12/949,609

(22) Filed: Nov. 18, 2010

(65) Prior Publication Data

US 2012/0078341 A1      Mar. 29, 2012

Related U.S. Application Data

(60) Provisional application No. 61/386,337, filed on Sep. 24, 2010.

(51) Int. Cl.
*A61F 2/91* (2013.01)
*A61F 2/915* (2013.01)
*A61F 2/966* (2013.01)
*A61F 2/95* (2013.01)

(52) U.S. Cl.
CPC ............... *A61F 2/915* (2013.01); *A61F 2/966* (2013.01); *A61F 2002/91533* (2013.01); *A61F 2002/91541* (2013.01); *A61F 2002/91575* (2013.01); *A61F 2002/9522* (2013.01); *A61F 2230/0054* (2013.01); *A61F 2250/0036* (2013.01)

(58) Field of Classification Search
CPC . A61F 2002/91558; A61F 2/915; A61F 2/82; A61F 2/966; A61B 17/3417
USPC ......................... 623/1.15, 1.16, 1.12, 1.1, 1.11
See application file for complete search history.

(56) References Cited

U.S. PATENT DOCUMENTS

| 4,553,545 A | 11/1985 | Maass et al. |
| 4,760,849 A | 8/1988 | Kropf |
| 5,102,417 A | 4/1992 | Palmaz |
| 5,195,984 A | 3/1993 | Schatz |
| 5,201,757 A | 4/1993 | Heyn et al. |
| 5,275,622 A | 1/1994 | Lazarus et al. |

(Continued)

FOREIGN PATENT DOCUMENTS

| EP | 0221570 B1 | 1/1991 |
| EP | 0335341 B1 | 3/1992 |
| EP | 1304091 A2 | 4/2003 |

(Continued)

OTHER PUBLICATIONS

U.S. Appl. No. 12/911,604, filed Oct. 25, 2010; first named inventor: Stephen Kao.

(Continued)

*Primary Examiner* — Richard Louis
(74) *Attorney, Agent, or Firm* — Oliff PLC

(57) ABSTRACT

A stent includes expandable rings formed from a plurality of interconnected struts. A plurality of bridges couple adjacent rings together. The bridges are connected to adjacent rings at first and second connection points, and a first brace element is disposed therebetween. The first connection point is circumferentially offset relative to the second connection point so that the bridge is transverse to the longitudinal axis of the stent. The first brace element of one bridge engages an adjacent bridge or a brace element of the adjacent bridge when the corresponding adjacent rings are in the contracted configuration thereby providing additional support and rigidity to the stent to lessen buckling of the stent during loading onto a delivery catheter or during deployment therefrom.

32 Claims, 13 Drawing Sheets

(56) References Cited

U.S. PATENT DOCUMENTS

| | | | |
|---|---|---|---|
| 5,292,321 A | | 3/1994 | Lee |
| 5,443,500 A | | 8/1995 | Sigwart |
| 5,449,373 A | | 9/1995 | Pinchasik et al. |
| 5,449,382 A | | 9/1995 | Dayton |
| 5,451,233 A | | 9/1995 | Yock |
| 5,545,210 A | | 8/1996 | Hess et al. |
| 5,591,197 A | | 1/1997 | Orth et al. |
| 5,603,698 A | | 2/1997 | Roberts et al. |
| 5,649,949 A | | 7/1997 | Wallace et al. |
| 5,669,932 A | | 9/1997 | Fischell et al. |
| 5,693,085 A | | 12/1997 | Buirge et al. |
| 5,733,303 A | * | 3/1998 | Israel et al. ............... 623/1.15 |
| 5,743,873 A | | 4/1998 | Cai et al. |
| 5,755,776 A | | 5/1998 | Al-Saadon |
| 5,755,781 A | | 5/1998 | Jayaraman |
| 5,776,142 A | | 7/1998 | Gunderson |
| 5,810,872 A | | 9/1998 | Kanesaka et al. |
| 5,836,964 A | | 11/1998 | Richter et al. |
| 5,861,027 A | * | 1/1999 | Trapp ........................ 623/1.15 |
| 5,873,907 A | | 2/1999 | Frantzen |
| 5,893,887 A | | 4/1999 | Jayaraman |
| 5,902,333 A | | 5/1999 | Roberts et al. |
| 5,907,893 A | | 6/1999 | Zadno Azizi et al. |
| 5,922,005 A | | 7/1999 | Richter et al. |
| 5,925,061 A | * | 7/1999 | Ogi et al. ..................... 623/1.2 |
| 5,954,743 A | | 9/1999 | Jang |
| 6,042,597 A | | 3/2000 | Kveen et al. |
| 6,090,127 A | | 7/2000 | Globerman |
| 6,129,755 A | | 10/2000 | Mathis et al. |
| 6,190,403 B1 | | 2/2001 | Fischell et al. |
| 6,193,745 B1 | | 2/2001 | Fogarty et al. |
| 6,241,757 B1 | | 6/2001 | An et al. |
| 6,254,612 B1 | | 7/2001 | Hieshima |
| 6,261,318 B1 | | 7/2001 | Lee et al. |
| 6,264,690 B1 | | 7/2001 | Von Oepen |
| 6,352,552 B1 | | 3/2002 | Levinson et al. |
| 6,468,299 B2 | | 10/2002 | Stack et al. |
| 6,562,064 B1 | | 5/2003 | deBeer |
| 6,579,308 B1 | | 6/2003 | Jansen et al. |
| 6,585,758 B1 | | 7/2003 | Chouinard et al. |
| 6,599,314 B2 | | 7/2003 | Mathis |
| 6,602,281 B1 | | 8/2003 | Klein |
| 6,605,110 B2 | | 8/2003 | Harrison |
| 6,656,220 B1 | | 12/2003 | Gomez et al. |
| 6,682,554 B2 | | 1/2004 | Oepen et al. |
| 6,699,278 B2 | | 3/2004 | Fischell et al. |
| 6,716,238 B2 | | 4/2004 | Elliott |
| 6,749,629 B1 | | 6/2004 | Hong et al. |
| 6,761,731 B2 | * | 7/2004 | Majercak ..................... 623/1.11 |
| 6,776,793 B2 | | 8/2004 | Brown et al. |
| 6,799,357 B2 | | 10/2004 | Webb et al. |
| 6,849,084 B2 | | 2/2005 | Rabkin et al. |
| 6,878,162 B2 | * | 4/2005 | Bales et al. ................. 623/1.15 |
| 6,929,660 B1 | | 8/2005 | Ainsworth et al. |
| 6,955,688 B2 | | 10/2005 | Wilson et al. |
| 7,122,049 B2 | | 10/2006 | Banas et al. |
| 7,131,993 B2 | * | 11/2006 | Gregorich .................... 623/1.16 |
| 7,137,993 B2 | | 11/2006 | Acosta et al. |
| 7,163,553 B2 | | 1/2007 | Limon |
| 7,252,679 B2 | | 8/2007 | Fischell et al. |
| 7,344,560 B2 | | 3/2008 | Gregorich et al. |
| 7,520,890 B2 | | 4/2009 | Phillips |
| 7,556,644 B2 | | 7/2009 | Burpee |
| 7,594,927 B2 | | 9/2009 | Majercak et al. |
| 7,611,531 B2 | | 11/2009 | Calisse |
| 7,722,661 B2 | | 5/2010 | Lenz et al. |
| 2001/0044650 A1 | | 11/2001 | Simso et al. |
| 2002/0045935 A1 | | 4/2002 | Jang |
| 2002/0082682 A1 | | 6/2002 | Barclay et al. |
| 2002/0120323 A1 | | 8/2002 | Thompson et al. |
| 2002/0188347 A1 | | 12/2002 | Mathis |
| 2003/0014101 A1 | | 1/2003 | Harrison |
| 2003/0040771 A1 | | 2/2003 | Hyodoh et al. |
| 2003/0097172 A1 | | 5/2003 | Shalev et al. |
| 2003/0109887 A1 | | 6/2003 | Galdonik et al. |
| 2003/0114920 A1 | | 6/2003 | Caro et al. |
| 2003/0130726 A1 | | 7/2003 | Thorpe et al. |
| 2003/0139797 A1 | * | 7/2003 | Johnson et al. ............... 623/1.13 |
| 2003/0195609 A1 | | 10/2003 | Berenstein et al. |
| 2004/0006381 A1 | | 1/2004 | Sequin et al. |
| 2004/0088044 A1 | | 5/2004 | Brown et al. |
| 2004/0147997 A1 | | 7/2004 | Gittings |
| 2004/0158247 A1 | | 8/2004 | Sitiso et al. |
| 2004/0158312 A1 | | 8/2004 | Chouinard et al. |
| 2004/0167609 A1 | * | 8/2004 | Majercak .................... 623/1.15 |
| 2004/0172128 A1 | | 9/2004 | Hong et al. |
| 2004/0186556 A1 | | 9/2004 | Hogendijk et al. |
| 2004/0186560 A1 | | 9/2004 | Alt |
| 2004/0204752 A1 | | 10/2004 | Ehr et al. |
| 2004/0220585 A1 | | 11/2004 | Nikolchev |
| 2004/0267353 A1 | | 12/2004 | Gregorich |
| 2005/0015136 A1 | | 1/2005 | Ikeuchi et al. |
| 2005/0055080 A1 | | 3/2005 | Istephanous et al. |
| 2005/0107863 A1 | | 5/2005 | Brown |
| 2005/0131516 A1 | | 6/2005 | Greenhalgh |
| 2005/0143806 A1 | | 6/2005 | Phillips |
| 2005/0288764 A1 | | 12/2005 | Snow et al. |
| 2006/0015173 A1 | * | 1/2006 | Clifford et al. .............. 623/1.16 |
| 2006/0020322 A1 | * | 1/2006 | Leynov et al. ............... 623/1.15 |
| 2006/0106452 A1 | * | 5/2006 | Niermann ................... 623/1.15 |
| 2006/0116751 A1 | | 6/2006 | Bayle et al. |
| 2006/0142849 A1 | * | 6/2006 | Killion et al. ............... 623/1.31 |
| 2006/0247759 A1 | | 11/2006 | Burpee et al. |
| 2007/0055348 A1 | | 3/2007 | Pryor |
| 2007/0129786 A1 | * | 6/2007 | Beach et al. ................. 623/1.15 |
| 2007/0185563 A1 | | 8/2007 | Zarbatany et al. |
| 2007/0213810 A1 | | 9/2007 | Newhauser et al. |
| 2007/0219618 A1 | | 9/2007 | Cully et al. |
| 2007/0255387 A1 | | 11/2007 | Kramer et al. |
| 2008/0103584 A1 | | 5/2008 | Su et al. |
| 2008/0109068 A1 | | 5/2008 | Fischell et al. |
| 2008/0125849 A1 | | 5/2008 | Burpee et al. |
| 2008/0208319 A1 | * | 8/2008 | Rabkin et al. ............... 623/1.16 |
| 2008/0215129 A1 | | 9/2008 | Venturelli et al. |
| 2008/0294240 A1 | * | 11/2008 | Casey ........................ 623/1.16 |
| 2008/0306581 A1 | | 12/2008 | Berglund et al. |
| 2009/0024205 A1 | | 1/2009 | Hebert et al. |
| 2009/0036976 A1 | | 2/2009 | Beach et al. |
| 2009/0118810 A1 | | 5/2009 | Klein et al. |
| 2009/0163989 A1 | | 6/2009 | Contiliano et al. |
| 2009/0182407 A1 | | 7/2009 | Leanna et al. |
| 2009/0210049 A1 | | 8/2009 | Thielen et al. |
| 2009/0228088 A1 | | 9/2009 | Lowe et al. |
| 2009/0264978 A1 | | 10/2009 | Dieck et al. |
| 2010/0004730 A1 | | 1/2010 | Benjamin et al. |
| 2010/0023106 A1 | | 1/2010 | Meyer et al. |
| 2010/0057187 A1 | | 3/2010 | Caldarise et al. |
| 2010/0094405 A1 | | 4/2010 | Cottone |
| 2010/0137973 A1 | | 6/2010 | Sutermeister et al. |
| 2010/0294287 A1 | | 11/2010 | Raju et al. |
| 2011/0106237 A1 | | 5/2011 | Bonsignore et al. |
| 2011/0230957 A1 | | 9/2011 | Bonsignore et al. |
| 2011/0307049 A1 | | 12/2011 | Kao |
| 2012/0078344 A1 | * | 3/2012 | Kao ............................ 623/1.16 |

FOREIGN PATENT DOCUMENTS

| | | |
|---|---|---|
| JP | H08-206226 A | 8/1996 |
| JP | 2001-509702 A | 7/2001 |
| JP | 2003-190294 A | 7/2003 |
| JP | 2004-255186 A | 9/2004 |
| JP | 2008-544765 A | 12/2008 |
| JP | 2009-529939 A | 8/2009 |
| WO | WO 98/38945 A1 | 9/1998 |
| WO | WO 00/16718 A1 | 3/2000 |
| WO | WO 00/28922 A1 | 5/2000 |
| WO | WO 00/57813 A1 | 10/2000 |
| WO | WO 03/051425 A2 | 6/2003 |
| WO | WO 2007/092276 A2 | 8/2007 |

OTHER PUBLICATIONS

U.S. Appl. No. 12/903,056, filed Oct. 12, 2010; first named inventor: Seshadri Raju.

(56) References Cited

OTHER PUBLICATIONS

Boston Scientific Corp.; Ultraflex} Tracheobronchial Stent System (product info.); retrieved from: <http://www.bostonscientific.com/templatedata/imports/collateral/PulmonaryEndoscopy/prospec_ultrfxtb_01_us.pdf>; 2 pgs.; © 2007 (year of publication is sufficiently earlier than the effective U.S. filing date and any foreign priority date).

Duerig et al.; An overview of superelastic stent design; Min Invas Ther & Allied Technol; vol. 9(3/4); pp. 235-246; (year of publication is sufficiently earlier than the effective U.S. filing date and any foreign priority date) 2000.

Malvé et al.; FSI analysis of the coughing mechanism in a human trachea; Annals of Biomedical Engineering; vol. 38; No. 4; pp. 1556-1565; Apr. 2010.

Raju et al.; U.S. Appl. No. 11/944,094 entitled "Venous Stent," filed Nov. 21, 2007.

Raju et al.; U.S. Appl. No. 12/603,970 entitled "Venous Stent," filed Oct. 22, 2009.

Dec. 18, 2014 Office Action issued in Chinese Patent Application No. 201180056195.6.

Jul. 6, 2015 Office Action issued in U.S. Appl. No. 13/244,151.

Jul. 28, 2015 Office Action issued in Japanese Patent Application No. 2013-530376.

Nov. 4, 2015 Search Report issued in European Patent Application No. 11827664.1.

\* cited by examiner

STENT WITH SUPPORT BRACES

CROSS-REFERENCES TO RELATED APPLICATIONS

The present application is a non-provisional of, and claims the benefit of priority of U.S. Provisional Patent Application No. 61/386,337 filed Sep. 24, 2010, the entire contents of which are incorporated herein by reference.

BACKGROUND OF THE INVENTION

1. Field of the Invention

The present invention relates generally to medical devices, and more particularly to endoluminal prostheses such as stents, or other implantable structures.

The prostheses may be placed in the arterial system, the venous system, or any other portion of the body. The use of stents may also be used to deliver drugs to tissue, support tissue, or maintain patency of body lumens, as well as performing other functions, and have been widely reported in the scientific and patent literature.

Stents are typically delivered via a catheter in an unexpanded configuration to a desired location in the body. The combined stent and catheter is typically referred to as the stent delivery system. Once at a desired location, the stent is expanded and implanted into the body lumen. Examples of locations in the body include, but are not limited to, arteries (e.g. aorta, coronary, carotid, cranial, iliac, femoral, etc.), veins (e.g. vena cava, jugular, iliac, femoral, hepatic, subclavian, brachiocephalic, azygous, cranial, etc.), as well as other locations including the esophagus, biliary duct, trachea, bronchials, duodenum, colon, and ureter.

Typically, a stent will have an unexpanded configuration with reduced diameter for delivery and an expanded configuration with expanded diameter after placement in the vessel, duct, or tract. Some stents are self-expanding, and some stents are mechanically expanded with a radial outward force applied from within the stent (e.g. with a balloon). Some stents have one or more characteristics common to both self-expanding and mechanically expandable stents.

Self-expanding stents are made from a material that is resiliently biased to return to a pre-set shape. These materials may include superelastic and shape memory materials that can expand to an implanted configuration upon delivery or through a change in temperature. Self-expanding stents are constructed from a wide variety of materials including nitinol (a nickel titanium alloy), spring steel, shape-memory polymers, etc.

In many stent delivery systems, particularly those used to deliver a self-expanding stent, the stent is typically retained on the catheter in its unexpanded form with a constraining member or other retention device such as a sheath or outer shaft. The stent may be deployed by retracting the outer shaft from over the stent. To prevent the stent from being drawn longitudinally with the retracting shaft, many delivery systems provide the catheter shaft with a pusher, bumper, hub, holder or other stopping element.

Precise delivery of stents can be challenging. In the case of balloon expandable stents, the stent may foreshorten as the stent radially expands, therefore, the change in length must be taken into account when deploying the stent at the treatment site. In the case of self-expanding stents, due to the elastic nature of the stents, they may "jump" away from the delivery catheter during deployment. Additionally, depending on the anatomy being treated, this may add further challenges to accurate stent delivery. In certain parts of the anatomy, longer stents may be needed to treat longer lesions or treatment regions. For example, with ilio-femoral and ilio-caval stenting, much longer stents are often required as compared with stenting of coronary lesions. This type of venous stenting may be used for the treatment of iliac vein compression syndrome (IVCS) and post-thrombotic syndrome (PTS) whereby the profunda and the inferior vena cava can be partially or completely blocked (or "stent jailed") by the stent if the stent is not placed accurately after deployment. Because the stents are longer, they are often more difficult to load and onto a delivery catheter, and they may buckle during the loading process when a radial force is applied to the stent to reduce its diameter.

Additionally, deployment forces of radially strong or large diameter self expanding stents can be relatively high. Furthermore, deployment forces can be equally high with stents that are longer in length due to the added friction between stent and a constraining or protective sheath. These high deployment forces may cause the stent to axially or radially buckle when loaded or deployed because the longer stents are less supported and less rigid, they can also buckle during deployment. This is of particular concern when long self-expanding stents are used.

Providing a stent that avoids or has reduced potential for buckling during delivery allows the stent to overcome the excessive friction and avoid the bind up of the device during stent release. This is also desirable since incomplete or incorrect release of stent may require the user to remove the delivery system from the body at which time the stent may be unintentionally deployed in an undesirable location.

Therefore, it would be desirable to provide a stent used for treating longer lesions or longer treatment regions that has greater structural support and rigidity in order to resist buckling or unwanted deformation during loading onto a delivery system or during deployment in a patient.

At least some of these objectives will be met by the inventions described herein.

2. Description of the Background Art

Relevant patents and publications include U.S. Pat. Nos. 5,755,776; 6,261,318; 6,605,110; 6,749,629; 6,929,660; 7,122,049; 7,611,531; 7,722,661; and U.S. Patent Publication Nos. 2004/0204752; 2005/0116751; 2007/0055348; 2007/0255387; and 2009/0163989.

BRIEF SUMMARY OF THE INVENTION

The present invention relates generally to medical devices, and more particularly to endoluminal prostheses such as stents, or other implantable structures. The stents may be deployed in the arterial system, the venous system, or any other portion of the body.

In a first aspect of the present invention, a stent comprises a plurality of radially expandable rings each having a contracted configuration suitable for delivery and a radially expanded configuration for engaging and supporting tissue. Each ring is formed from a plurality of interconnected struts, with adjacent struts in each ring being connected together with a connector, and each ring having a proximal end, and a distal end. The plurality of rings are coaxially aligned with one another to form a longitudinal axis. A distal end of one ring faces a proximal end of an adjacent ring. The stent also has a plurality of bridges disposed between adjacent rings. The plurality of bridges couple adjacent rings together. One or more of the bridges comprise a first end, a second end, and a first brace element therebetween. The first end of the bridge is coupled with the distal end of a first ring at a first connection point, and the second end of the bridge is coupled with the proximal end of an adjacent second ring at a second connection point. The first connection point may be circumferentially offset relative to the second connection point so that the bridge is transverse to the longitudinal axis. The first brace element of one bridge engages an adjacent bridge or a brace element of the adjacent bridge when the corresponding adjacent rings are in the contracted configuration thereby providing additional support and rigidity to the stent to lessen buckling of the stent during loading onto a delivery catheter or during deployment therefrom.

The plurality of interconnected struts may form a series of peaks and valleys. The peaks and valleys of a first ring may be in phase with the peaks and valleys of an adjacent ring. The connector that interconnects the plurality of struts may be U-shaped or V-shaped. The rings may be self-expanding, balloon expandable, or a combination thereof.

The one or more bridges may comprise a first arm and a second arm, and the brace may be disposed therebetween. The first arm or the second arm may comprise a linear strut. The first arm or the second arm may comprise a width, and the first brace element may comprise a width wider than the width of the first or second arm. The first connection point may be a peak of one ring, and the second connection point may be on a valley of an adjacent ring. The first connection point may be on the apex of the peak, and the second connection point may be on the bottom of the valley.

A bridge element may couple each pair of adjacent struts interconnected together in a first ring with a pair of adjacent struts interconnected together in an adjacent second ring or an adjacent third ring. The first brace element may comprise a rectangular region, and may also comprise an upper engagement surface and a lower engagement surface. The upper engagement surface may engage a lower engagement surface on an adjacent brace element when the corresponding rings are in the collapsed configuration. The upper and lower engagement surfaces may comprise flat planar surfaces. The upper engagement surface may have a first contour and the lower engagement surface on the adjacent brace may have a second contour, and the first contour may nest within the second contour.

The one or more bridges may comprise a plurality of bridges each having a brace element. The bridges may join the two adjacent rings together, and the brace elements on each bridge may be axially aligned with one another to form a circumferentially oriented column of braces. The brace elements on each bridge may be circumferentially aligned with one another to form an axially oriented row of braces. The brace on a first bridge may be axially offset relative to a brace on the adjacent ring thereby forming a staggered pattern of braces. The braces may also be arranged to form a circumferentially staggered pattern.

A first bridge may couple a first ring and a second adjacent ring, and a second bridge may couple the second ring with a third ring adjacent the second ring. The first bridge may have a first slope, and the second bridge may have a second slope opposite the first bridge. The first brace element may not contact a brace element of an adjacent bridge when the corresponding rings are in the radially expanded configuration. The plurality of bridges may be disposed between adjacent rings and may be substantially parallel with one another.

One or more of the bridges may comprises a length, and the first brace element comprises a length shorter than the bridge length. The one or more bridges may comprise a second brace element or a plurality of brace elements, and the brace elements may be separated from the first bridge by a strut. The one or more bridges may comprise a plurality of bridges each having a first brace and a second brace separated by a strut.

The plurality of bridges may join two adjacent rings together, and the first and second brace elements on each bridge may be circumferentially aligned with one another, thereby forming a first column of circumferentially oriented brace elements and a second column of circumferentially oriented brace elements.

The first brace element may comprise a slotted region extending through the entire thickness of the brace element. The first brace element may comprise a solid tab without slots extending therethrough. A pair of bridges each having a brace element and joining two adjacent rings may be separated by a bridge without a brace element and joining the two adjacent rings. At least some of the plurality of interconnected struts may remain unconnected with a bridge. At least some of the bridges may comprise a brace element having a tapered proximal or distal end.

In another aspect of the present invention, a method for delivering a prosthesis may comprise providing a stent comprising a plurality of radially expandable rings interconnected with a plurality of bridges, wherein some of the bridges comprise a brace element. The stent is loaded onto a delivery catheter, and is supported during the loading. Supporting the stent may comprise engaging brace elements on adjacent bridges against one another. The stent is deployed from the delivery catheter.

Loading the stent may comprise crimping the stent onto the delivery catheter. The stent may comprise a diameter, and the crimping step may reduce the diameter. Loading the stent may comprise applying a radial force against the stent.

Each brace element may comprise an upper surface and a lower surface, and engaging brace elements may comprise nesting the upper surface of one brace element with a lower surface of an adjacent brace element. Supporting the stent may reduce or eliminate buckling of the stent during loading.

Deploying may comprise retracting a sheath away from the stent so that the stent is unconstrained from radial expansion. Deploying may comprise self-expanding the stent or balloon expanding the stent. Deploying the stent may comprise deploying the stent into a vein to alleviate compression of a portion of the vein.

The method may further comprise rigidifying the stent during the deployment. Rigidifying may comprise engaging brace elements on adjacent bridges against one another. Rigidifying may comprise applying an axially oriented force to the stent, thereby resulting in the engagement. Rigidifying the stent may reduce or eliminate buckling of the stent during deployment.

The engaged brace elements may disengage from one another during or after the deployment.

These and other embodiments are described in further detail in the following description related to the appended drawing figures.

DETAILED DESCRIPTION OF THE INVENTION

Figure 1:
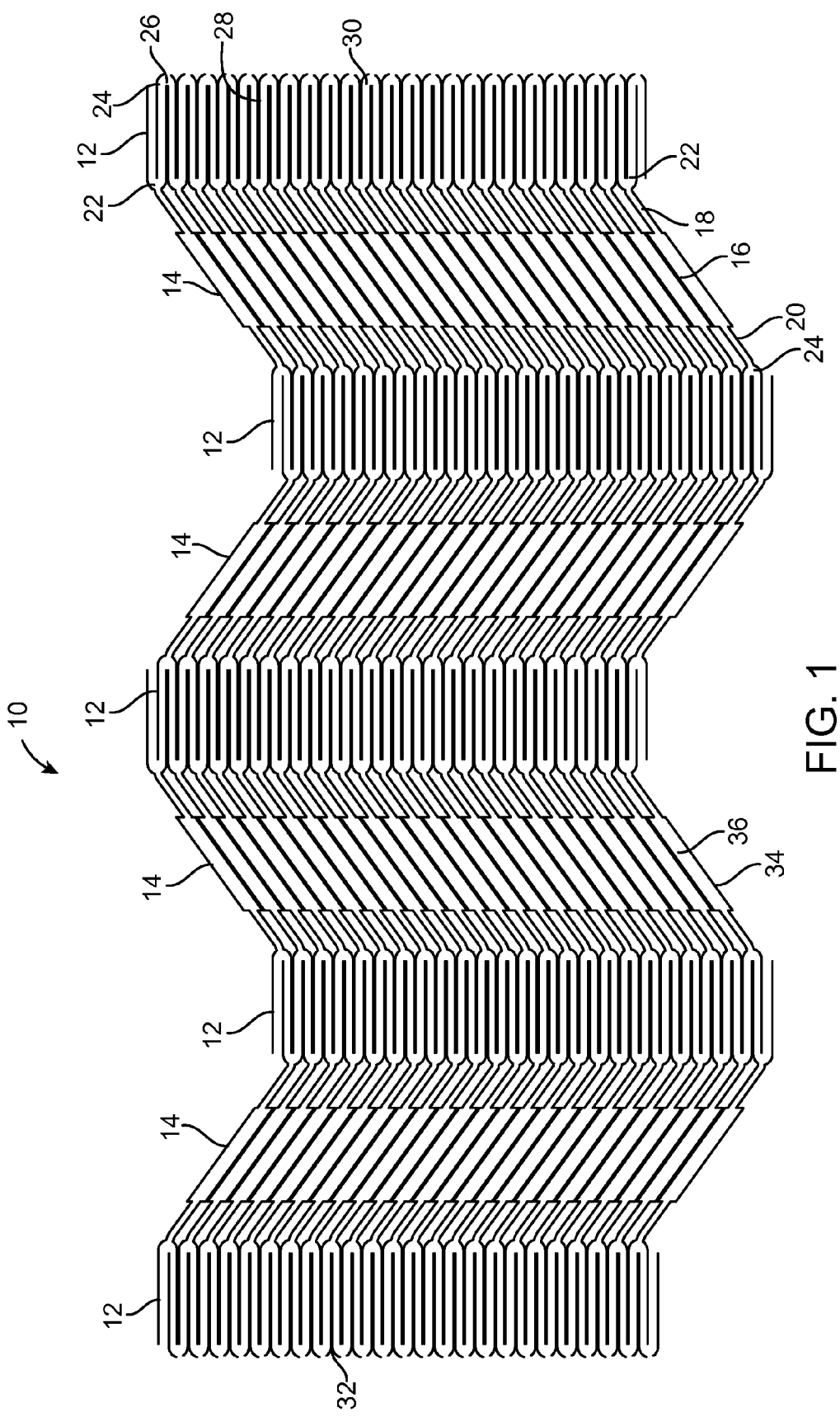
FIG. 1 illustrates an exemplary embodiment of a braced stent in a radially collapsed configuration.

The present invention relates generally to medical devices, and more particularly to endoluminal prostheses such as stents, or other implantable structures. The stents may be placed in the arterial system, the venous system, or any other portion of the body. The stents may also be used to deliver drugs to tissue, support tissue, or maintain patency of bodily lumens, as well as performing other functions, and have been widely reported in the scientific and patent literature.

As discussed above, longer stents may buckle or undesirably collapse due to lack of rigidity or support. Modeling of typical stents which have a series of rings connected together with a bridge shows that material tensile strength, bridge width, stent wall thickness, and bridge length are key factors that determine the buckling force the bridge can withstand before deformation occurs. The column strength (F) of the stent may be mathematically represented using the following equation where L is the length of the bridge, b is the wall thickness of the stent, h is the bridge width. Additionally, E is the stent material modulus of elasticity, I is the second moment of interia, and K is a column effective length factor, where the value depends on conditions of end support of the column.

$$F = \pi^2 EI/(KL)^2, \text{ and } I = bh^3/12$$

Therefore, adding a brace element to the bridge widens the bridge which increases the bridge second moment of inertia, thereby increasing the column strength of the stent. Additionally, one of skill in the art will appreciate that column strength or buckling force may also be increased by effectively shortening the length L of the bridges when braces are included.

The outward force of the stent is a function of its material properties, architecture, diameter, and other service conditions. Expandable stents are commonly formed from a series of expandable ring members, each of which is comprised of a series of strut elements disposed around the circumference of the structure. The longitudinal connections between these expandable ring members can be described as bridging members. The number, design, order, and connection of these expandable ring members and bridging members defines the overall architecture of the stent. The strength, stiffness, conformability, and flexibility of the stent are controlled by the selection and design of these expandable ring members and bridging members.

The stiffness or strength of the stent is strongly influenced by the design of the expandable ring members. An expandable ring member is commonly comprised of a series of n strut elements disposed around the circumference of the structure. Each strut can be further described by its length L, width w, and thickness t. The stiffness of the stent k can be approximated using a formula relating n, L, w, t, and the elastic modulus of the material, E. Vascular stents may be subjected to two different types of loading conditions in vivo. The first of these can be described as hoop, circumferential, or radial loading. An arterial or venous stent placed in a perfectly concentric lesion is an example of this type of loading. The stiffness of a stent subjected to such a hoop load can be approximated by the following relationship.

$$k_{hoop} \alpha (Ew^3 t)/(nL^3)$$

Thus, in this mode of loading, it is clear that the hoop stiffness is dominated by the cube of the strut width, and inversely related to the cube of the strut length. Therefore, to increase stent stiffness, wider and shorter struts may be used.

FIG. 1 illustrates an exemplary embodiment of a braced stent that provides enhanced rigidity and support during loading and deployment. The stent 10 is typically a cylindrically shaped structure, and has a radially collapsed configuration for delivery, and a radially expanded configuration for engaging and supporting tissue. FIG. 1 shows stent 10 in the collapsed configuration (e.g. after loading or crimping onto a delivery catheter) after it has been unrolled and flattened out. The stent 10 has proximal end 30 and a distal end 32, and includes a plurality of annular rings 12 interconnected together and coaxially aligned with one another. The rings are connected together with a bridge element 14. The distal end of one ring generally faces the proximal end of an adjacent ring, and the proximal end of one ring generally faces the distal end of an adjacent ring (except for the proximal-most and distal-most rings). In this embodiment, each ring is formed from a plurality of interconnected struts 28 that form a series of peaks 22 and valleys 24. The peaks and valleys of one ring are preferably in-phase with the peaks and valleys of an adjacent ring, although this is not required and the rings may be out-of-phase with one another. The struts 28 are generally linear and generally parallel with the longitudinal axis of the stent 10, although this is not intended to be limiting. Adjacent pairs of struts 28 are coupled together with a connector element 26. The connector element is preferably V-shaped or U-shaped, although other geometries may also be used. The bridge element 14 includes a proximal arm 18, a distal arm 20, and a brace element 16 disposed therebetween. The proximal and distal arms 18, 20 are preferably linear struts, but any geometry may be used. The proximal arm 18 is preferably coupled to a connection point on the proximal ring, and the distal arm 20 is preferably coupled to a connection point on the distal ring. The proximal arm preferably is coupled to the apex of a peak 22, and the distal arm is preferably coupled to the bottom or nadir of a valley 24 on the adjacent distal ring. In this embodiment, the brace element is parallelogram shaped such that the width of the brace element is wider than the width of the arms 18, 20. The length of the brace element 16 is also less than the total length of the bridge 14, and the length of the brace element is longer than either the proximal or distal arm. The brace element has an upper surface 36 and a lower surface 34. In this embodiment, the upper and lower engagement surfaces are flat and planar, such that the upper surface engages the lower surface of an adjacent brace element on an adjacent bridge. The upper and lower surfaces engage one another in the radially collapsed configuration. This helps provide additional support and rigidity to the stent when it is crimped or otherwise loaded onto a stent delivery catheter and helps reduce or prevent the likelihood of buckling. While the preferred shape of the brace element is a parallelogram, one of skill in the art will appreciate that this is not intended to be limiting, and that other geometries may also be used, such as rhomboid, trapezoidal, non-quadrilateral, rectangular, square, circular, oval, elliptical, triangular, as well as other shapes and combinations thereof. Additionally, during stent deployment, a constraining or outer protective sheath may be retracted causing forces to be applied to the stent. Retraction of the sheath may apply axially oriented forces to the stent that can result in buckling during deployment of the stent. The axially oriented forces cause the brace elements to engage one another, thereby providing better support and rigidity to the stent during deployment, thereby reducing the likelihood of buckling of the stent. In alternative embodiments, the upper and lower engagement surfaces may not be flat or planar, but they may still be contoured such that one surface nests with the other surface, for example one surface being convex while the other is concave, seen in FIG. 13.

Figure 13:
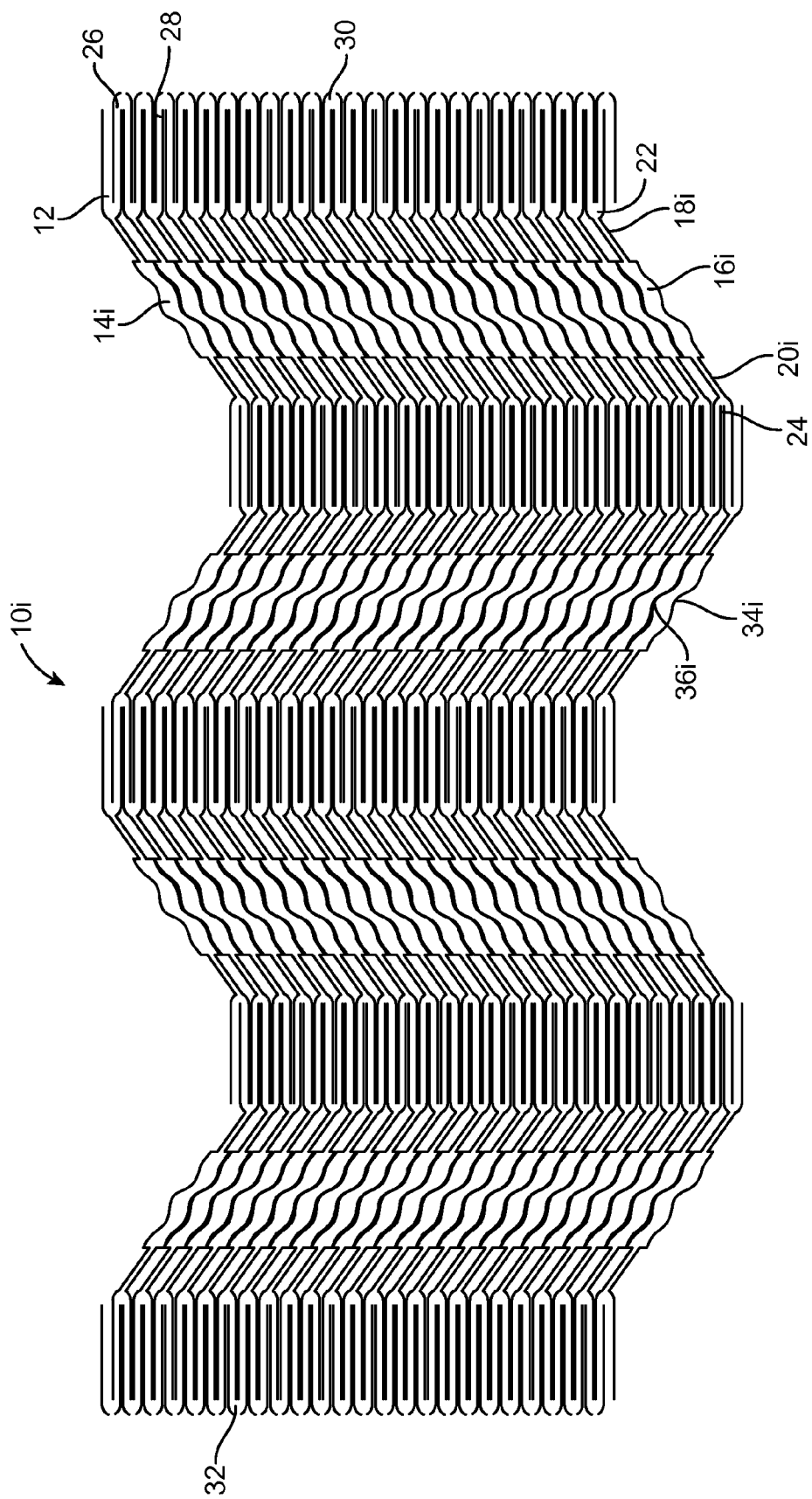
FIG. 13 illustrates an exemplary embodiment of a stent having brace elements with contoured engagement surfaces.

Referring to FIG. 13, stent 10i generally takes the same form as the other stents disclosed herein, with the major difference being that instead of the bridge having a brace element with flat planar upper and lower engagement surfaces, the bridge 14i has brace element 16i with an arcuate upper engagement surface 36i, and an arcuate lower engagement surface 34i. In this embodiment, the brace element 16i is disposed between proximal and distal arms 18i, 20i which are linear struts which couple the brace element 16i to the proximal and distal adjacent rings 12. The upper engagement surface 36i has a convex region surrounded by concave regions, and the lower engagement surface 34i has a concave region surrounded by convex regions. Thus, the convex region of the upper engagement surface will engage and nest with the concave region on an adjacent lower engagement surface when the stent is in the collapsed configuration. One of skill in the art will appreciate that other contoured surfaces may also be used to nest with one another.

Referring back to the embodiment of FIG. 1, a bridge having a brace element connects each peak on one ring with each valley on an adjacent ring. The proximal and distal connection points are circumferentially offset from one another such that the bridge is angled or transverse relative to the longitudinal axis of the stent. FIG. 1 also illustrates how the slope of bridges alternate between adjacent rings. For example, the bridges generally have a positive slope between the first and second proximal-most rings, while the bridges between the second and third proximal-most rings have a negative slope. Additionally, the brace elements on bridges between adjacent rings are axially and circumferentially aligned so that the brace elements are substantially parallel with one another and aligned in a single circumferentially oriented column. This embodiment has five rings, and four columns of bridges. The stent may be balloon expandable, or in preferred embodiments is self-expanding. Balloon expandable stents are typically fabricated with 316L stainless steel, or cobalt chromium alloy, while self-expanding stents are often fabricated from a nickel titanium alloy such as nitinol. One of skill in the art will appreciate that other materials such as resilient polymers, biodegradable materials, or other materials may be used to fabricate the stent. The stent is preferably laser cut from a tube such as a hypotube, or it may be electrical discharge machined (EDM) from a tube, photochemically etched from a flat sheet rolled into a cylinder and welded together. It is preferably an integral component, although it may be fabricated from several segments that are coupled together (e.g. by welding or bonding).

Figure 2:
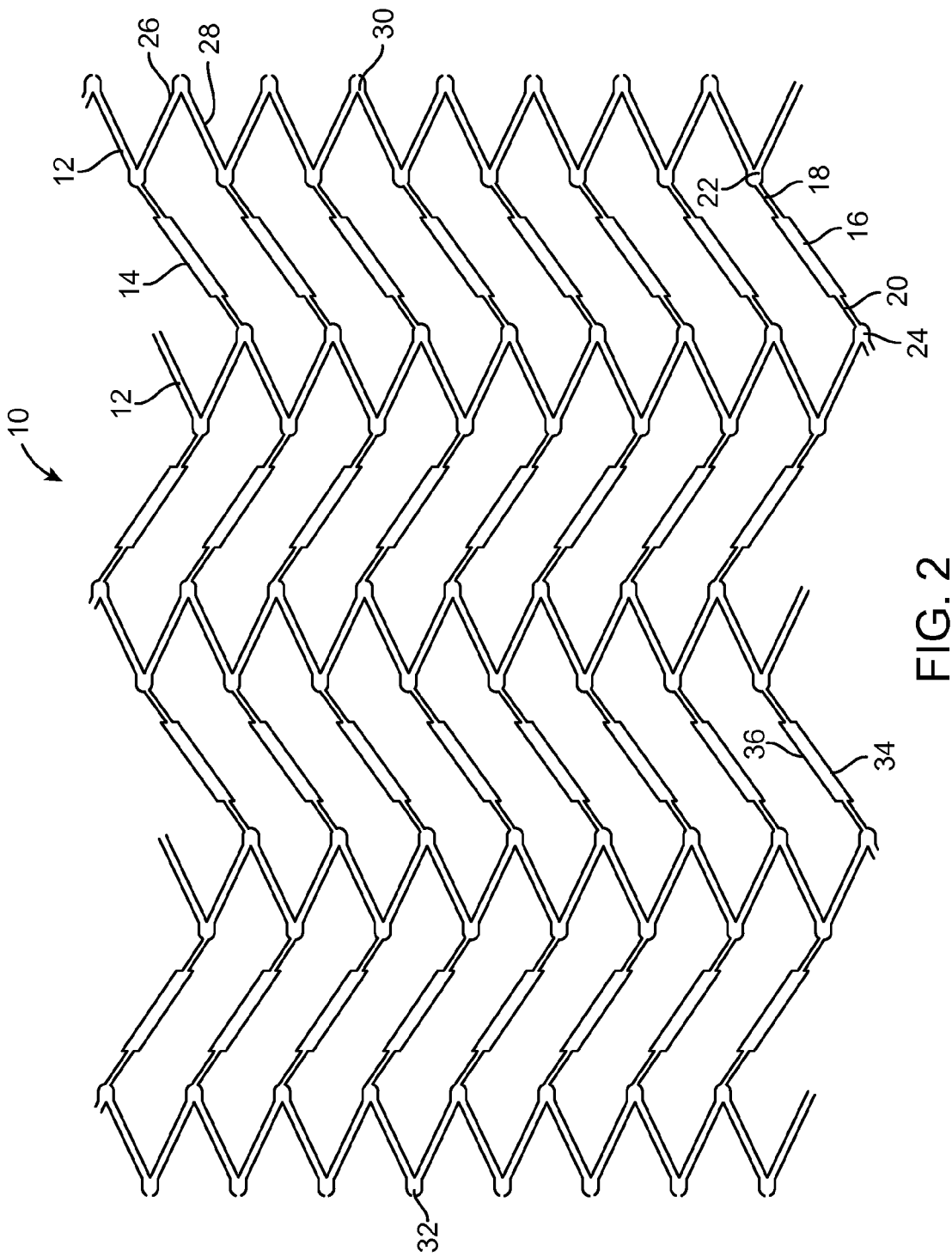
FIG. 2 illustrates the stent of FIG. 1 in a radially expanded configuration.

FIG. 2 illustrates the stent 10 of FIG. 1 in the radially expanded configuration. The rings 12 radially expand, therefore struts 28 open up and angulate away from the adjacent strut. This results in an increase in the stent diameter. Additionally, bridges 14 also move away from one another such that the upper engagement surface 36 no longer engages the lower engagement surface 34 of the adjacent brace. In the radially expanded configuration, the stent engages and supports tissue (e.g. supports a vessel wall). Therefore, the additional structural support in the compressed form from the braces contacting each other is lost when the stent is expanded because the contact between braces is no longer present. However, some added strength and rigidity remains in the expanded form due to the increase in bridge width in the braced areas.

Figure 3:
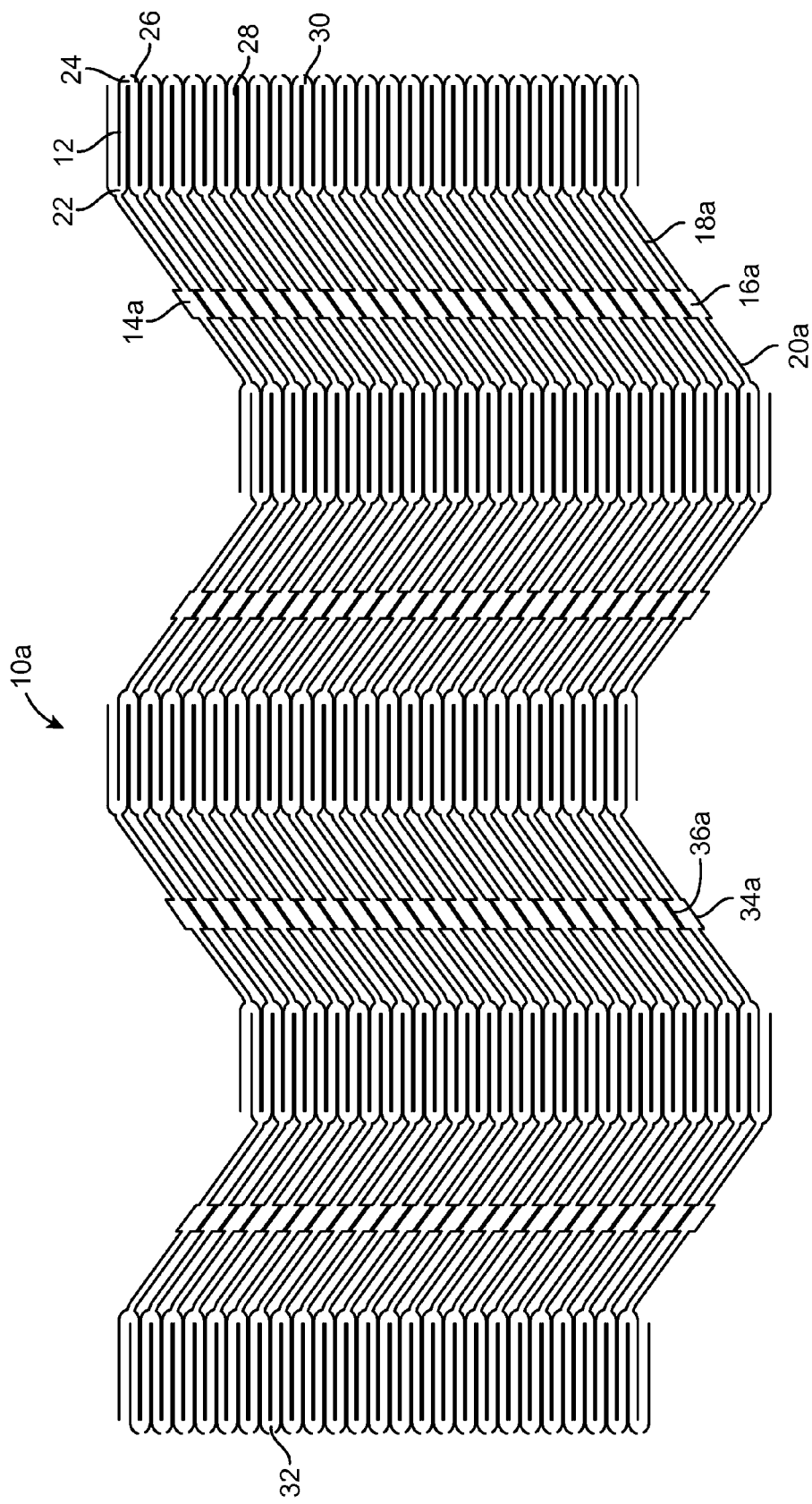
FIG. 3 illustrates another exemplary embodiment of a braced stent.

FIG. 3 illustrates another exemplary stent embodiment that is similar to the embodiment of FIG. 1, with the major difference being the brace element 16a on the bridge 14a. In this embodiment, the brace element 16a is shorter than the brace element 16 in FIG. 1, therefore upper and lower engagement regions 36a, 34a are still flat and planer, but correspondingly shorter in length. Other aspects of stent 10a generally takes the same form as stent 10 in FIG. 1. In this embodiment, the brace elements 14a are still parallelogram shaped, however, the length of the brace element 14a is shorter than either of the arms 20a, 18a on either side thereof. The width of the brace element is still wider than the width of arms 20a 18a. Brace elements 14a are aligned axially and circumferentially between adjacent rings so as to form a single column of aligned brace elements where upper and lower engagement surfaces engage the adjacent engagement surface of an adjacent brace element to provide additional rigidity and support to the stent during deployment or during loading onto a delivery system.

Figure 4:
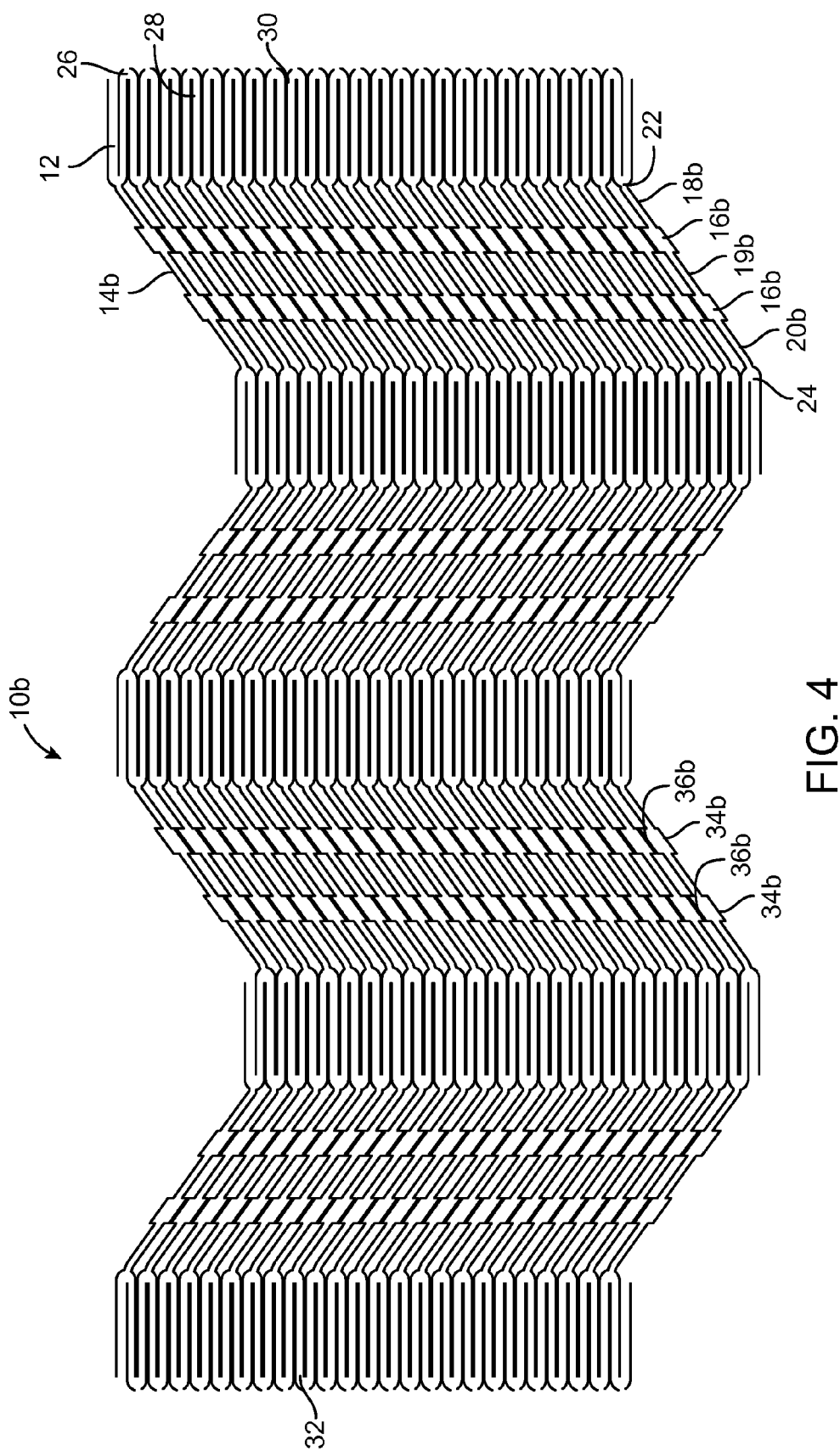
FIG. 4 illustrates still another exemplary embodiment of a braced stent having multiple braces on a bridge.

FIG. 4 illustrates another exemplary stent embodiment that is similar to the embodiment of FIG. 1, with the major difference being that the bridges each have two brace elements. In this embodiment, each bridge 14b includes three arms 18b, 19b, 20b formed from linear struts. A brace element 16b is disposed between adjacent arms. Thus arm 18b is coupled preferably to the apex of a peak 22 on one ring, and arm 20b is preferably coupled to the nadir of a valley 24 on the adjacent ring. Two brace elements 16b are coupled to arms 18b, 20b, and disposed between adjacent rings. A third arm 19b separates the two brace elements 16b. In this embodiment, both brace elements are the same geometry, here parallelogram shaped, however in alternative embodiments the brace elements may be different from one another. In this embodiment, the width of each brace element is wider than the width of the struts forming the arms, and the length of each brace element is less than the length of each arm. The brace elements are circumferentially and axially aligned so as to form two columns of aligned brace elements. Also, in this embodiment, the bridges will have two upper and two lower engagement surfaces 34b, 36b that engage the adjacent engagement surface in an adjacent bridge when the stent is radially collapsed or an axially oriented force is applied thereto. As in the other embodiments described herein, this helps stabilize the stent and rigidify the stent during loading onto a delivery system or during delivery. Other aspects of this embodiment generally take the same form as the embodiments in FIGS. 1-3 above.

Figure 5:
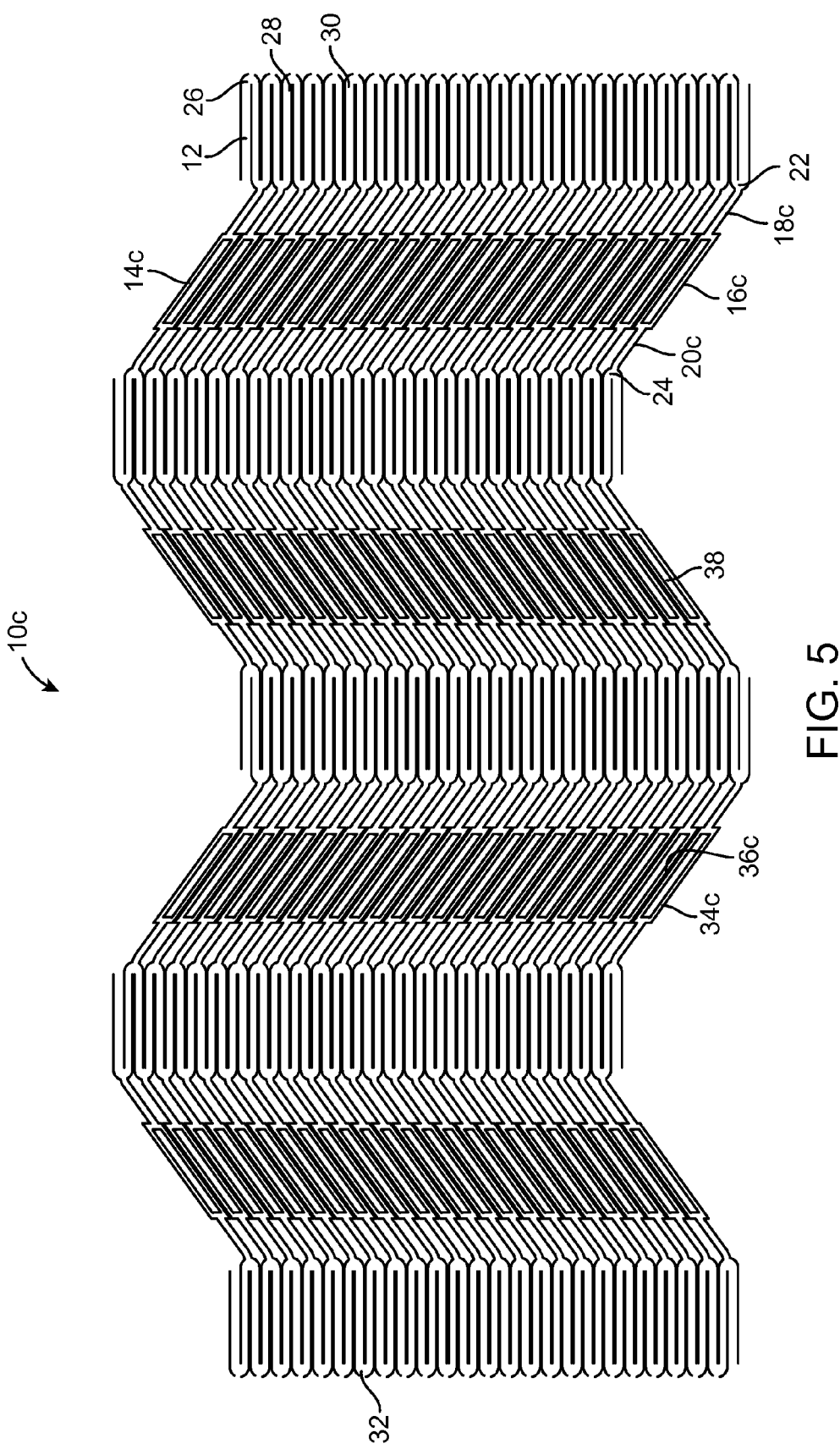
FIG. 5 illustrates an exemplary embodiment of a braced stent having a brace element with a slotted region.

FIG. 5 illustrates another exemplary embodiment of a braced stent 10c. The stent 10c is similar to previous embodiments, with the major difference being that the brace element 16c is not solid, and has a slotted region 38 extending through the thickness of the brace. The slotted region 38 is preferably rectangular or parallelogram shaped and it may be laser cut, EDM machined, photochemically etched, or otherwise formed in the stent so that the brace element has upper and lower elongate linear struts that form the upper and lower engagement surfaces 36c, 34c for engaging an adjacent engagement surface on an adjacent brace element. The brace element 16c is coupled to two arms 18c, 20c which are formed from linear struts that are connected to an adjacent peak 22 and valley 24 on adjacent rings 12. Brace elements 16c are axially and circumferentially aligned with one another to form a single aligned column of brace elements disposed between adjacent rings. Other aspects of stent 10c generally take the same form as those of embodiments previously described above. The geometry of the slotted region may be adjusted in order to provide the stent with desired mechanical properties.

Figure 6:
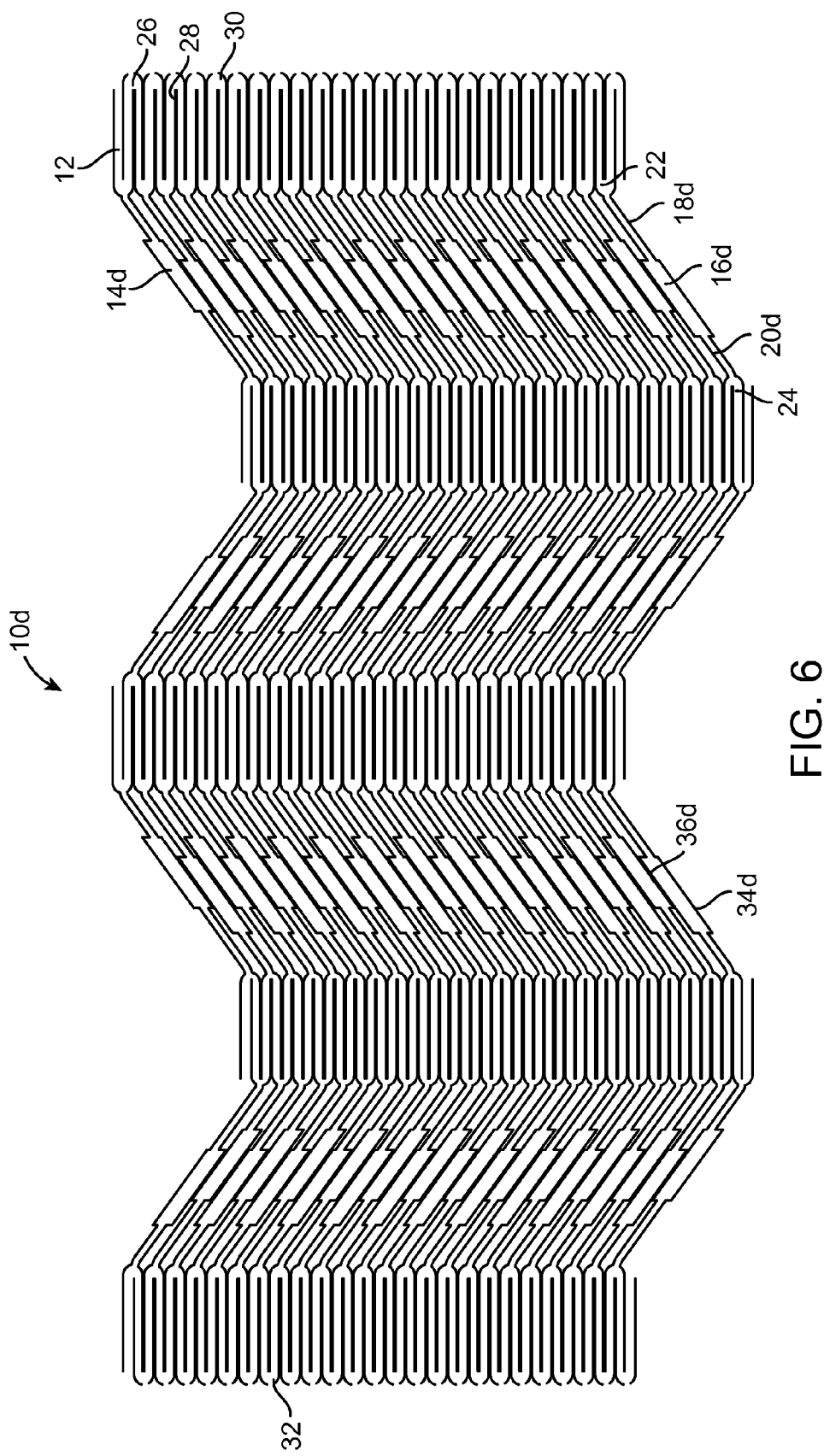
FIG. 6 illustrates an exemplary embodiment of a stent having staggered brace elements.

The embodiment of FIG. 6 is similar to previous embodiments, with the major difference being that instead of the brace elements being aligned to form a single aligned column of brace elements between adjacent rings, the brace elements are axially displaced relative to one another so that a staggered column of braces is formed between adjacent rings. Stent 10d generally takes the same form as the embodiments described above, but bridges 14d include a brace element 16d with upper and lower engagement surfaces 36d, 34d disposed between arms 18d, 20d formed from linear struts that are coupled to the peaks 22 and valleys 24 of adjacent rings 12. Each brace is axially displaced relative to an adjacent brace so that the brace elements 16d form an alternating or staggered column of brace elements 16d between adjacent rings. Thus, only a portion of the upper engagement surface 36d engages only a portion of the lower engagement surface 34d. The entire engagement surfaces do not contact one another in this embodiment. Other aspects of the stent 10d generally take the same form as those described above.

Figure 7:
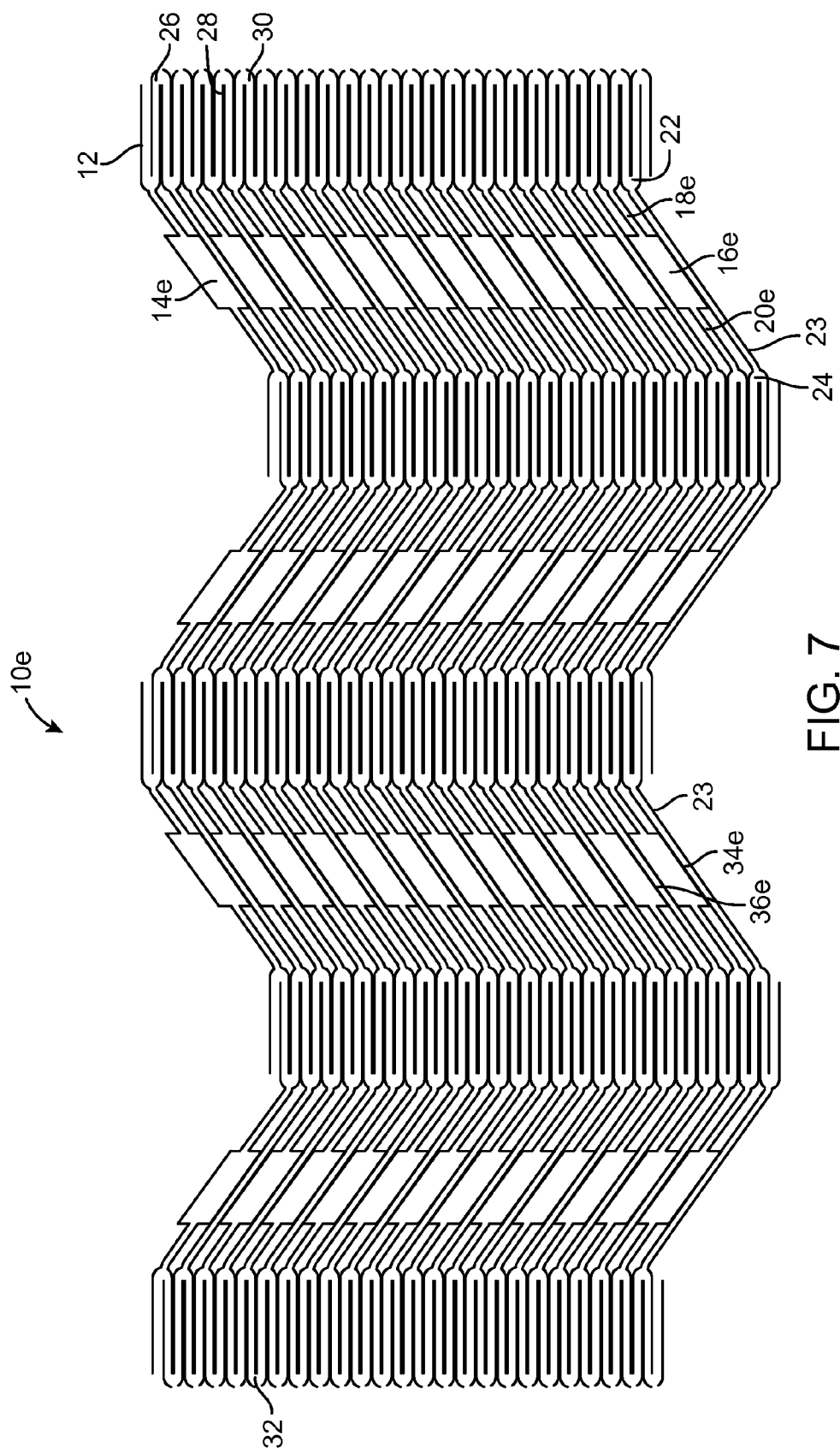
FIG. 7 illustrates an exemplary embodiment of a stent with alternating brace elements.

FIG. 7 illustrates another embodiment of a braced stent that is similar to those described above, with the major difference being that in this exemplary embodiment, the brace element is only on every other bridge between adjacent rings. Stent 10e generally takes the same form as those described above, except that every other bridge 14e includes a brace element 16e disposed between the two arms 18e, 20e, which are formed from linear struts connected to a peak 22 and a valley 24 on adjacent rings 12. A linear strut 23 is disposed between adjacent bridges 14e having brace elements, and one end of the linear strut 23 is coupled to a peak 22, while the opposite end is coupled to a valley 24. The brace elements 16e are aligned so as to form a single aligned column of brace elements between adjacent rings 12. The brace elements 16e are parallelogram shaped in this embodiment, but may be other shapes as well. The brace elements include an upper engagement surface 36e, and a lower engagement surface 34e that are both flat planar regions. Unlike other embodiments where an upper engagement surface engages a lower engagement surface of an adjacent brace element, in this embodiment the upper engagement surface engages an inferior surface of a linear strut 23 and the lower engagement surface engages a superior surface of a linear strut 23 when the stent is in a radially collapased configuration, such as when a radially inward force is applied to the stent, or when an axially oriented force is applied to the stent. The bridges 14e are generally parallel with one another, and the linear struts 23 are also generally parallel with one another. Just as in earlier embodiments the slope of the bridges alternates between a positive and negative slope, the slope of the linear strut 23 similarly alternates between a positive and negative slope. Additionally, because the brace elements are only on every other bridge, the brace element is wider than the width of the arms 18e, 20e, and the brace element is also wide enough to engage an adjacent brace element.

Figure 8:
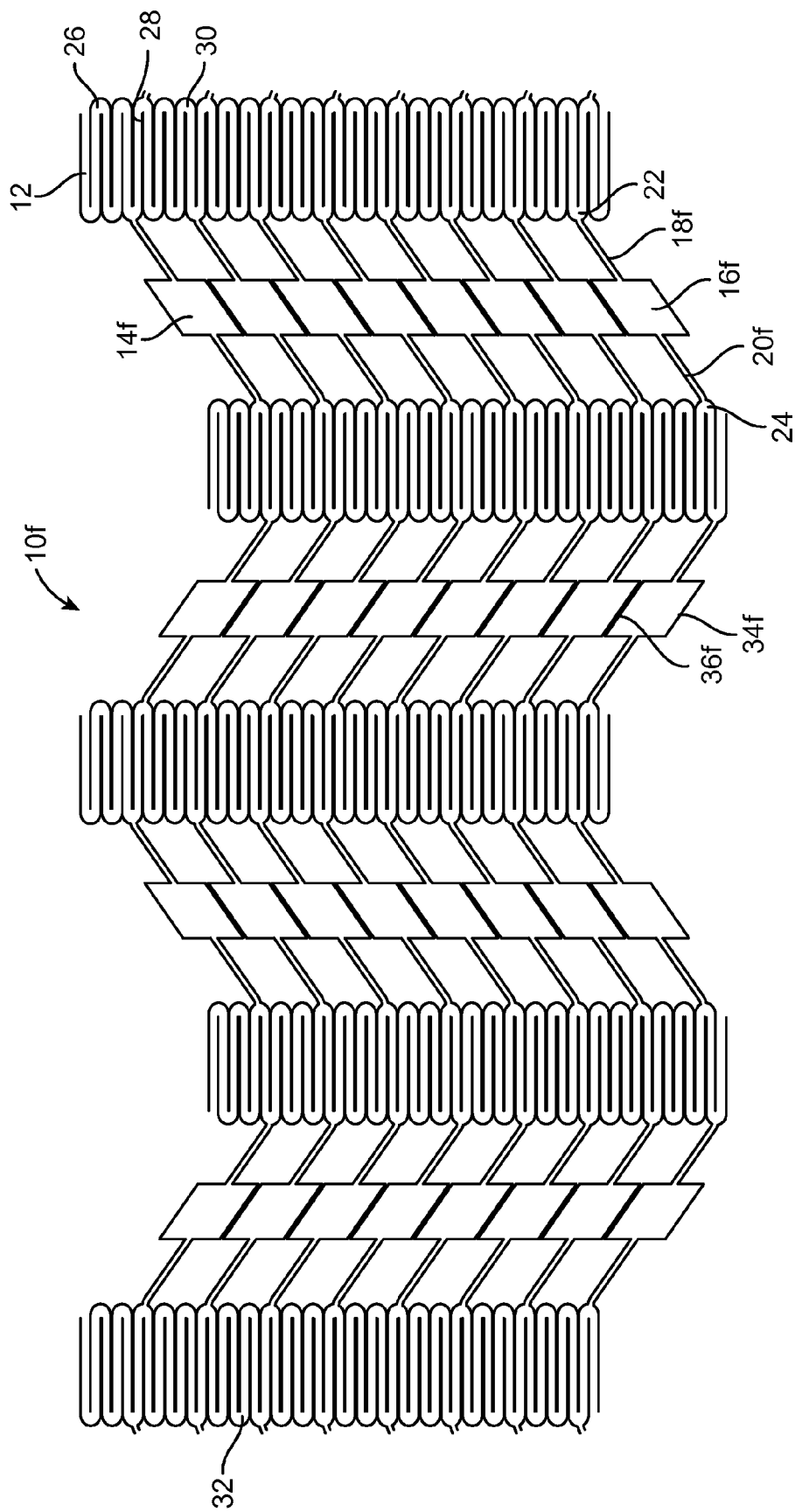
FIG. 8 illustrates another exemplary embodiment of a stent having alternating brace elements.

FIG. 8 illustrates another embodiment of a stent having braced connectors. Stent 10f is substantially similar to previous embodiments with the major difference being that in this embodiment, a bridge 14f only connects every third peak 22 to every third valley 24 of an adjacent ring 12. This requires fewer bridges than previous embodiments, and that may provide a stent that has greater flexibility between adjacent rings, and also reduces the amount of metal or other material that is implanted in a patient, while still providing the necessary support and rigidity to the stent during loading or deployment. Stent 10f generally takes the same form as previous stents described above, and has a plurality of interconnected rings 12. Adjacent rings are connected with a bridge 14f having arms 18f, 20f that are connected to a peak or valley 22, 24. Each bridge 14f includes a brace element 16f that generally has a parallelogram shape that is wider than the width of the arms 18f, 20f, and the length of the brace element 16f is shorter than the length of the linear struts which form arms 18f, 20f. The upper engagement surface 36f of a brace element engages the lower engagement surface 34f of an adjacent brace element. In this embodiment, the upper and lower engagement surfaces 34f, 36f are flat planar surfaces, although as describe above, the engagement surfaces may be contoured to nest with one another (e.g. a concave surface and a convex surface).

Figure 9:
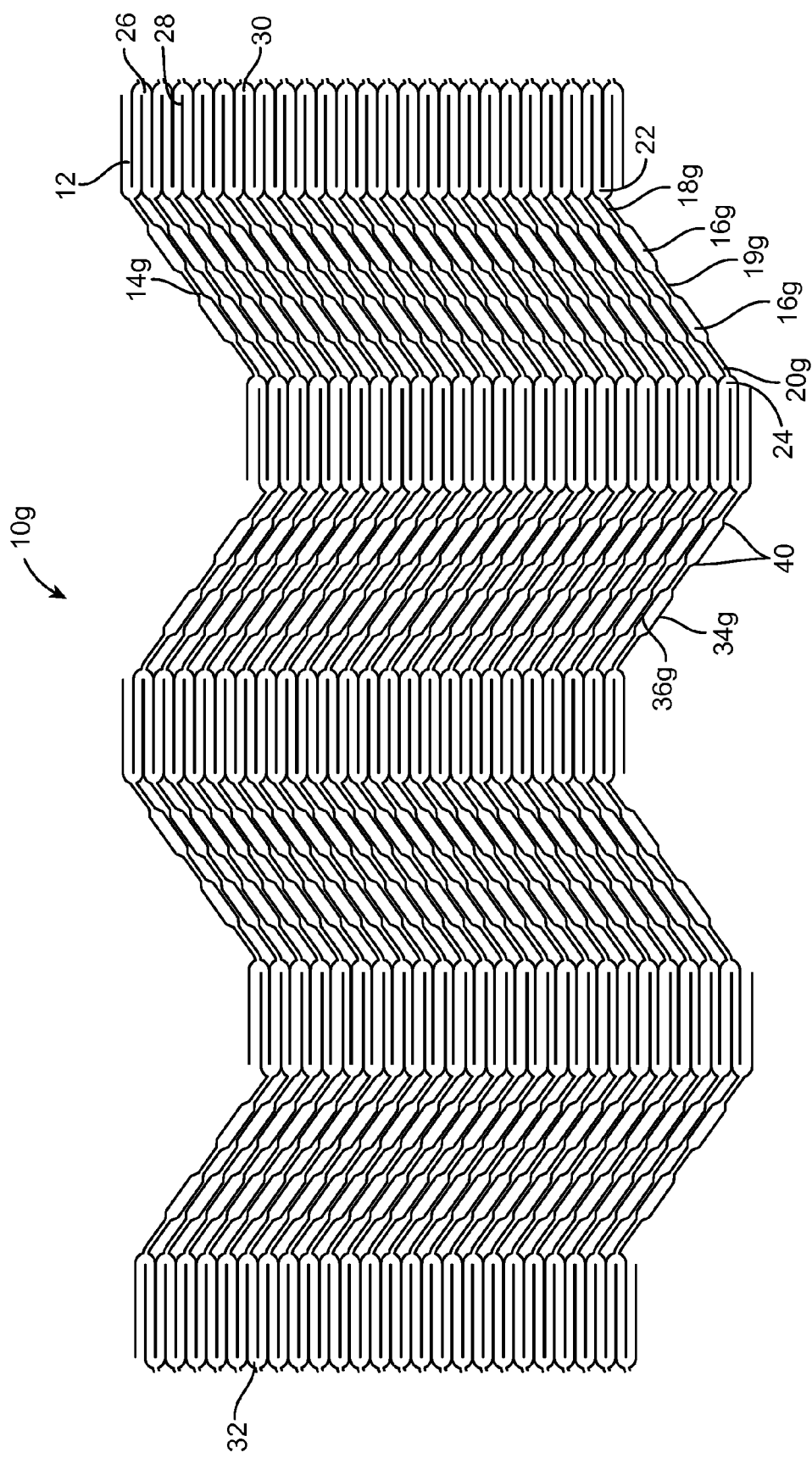
FIG. 9 illustrates still another exemplary embodiment of a stent having multiple brace elements on a connector.

FIG. 9 illustrates another embodiment of a braced stent. This embodiment is similar to the embodiment of FIG. 4, with the major difference being that the proximal and distal ends of each brace element are tapered thereby smoothing leading edges that potentially provide sharp edges which may cause trauma to the tissue, or may get hung on or damage a portion of the delivery catheter either during delivery or in the event the stent needs to be recaptured prior to full deployment. Stent 10g includes two brace elements on each bridge 10g. The bridge 10g includes three arms 18g, 19g, 20g. Arms 18g and 20g have one end coupled to a peak 22 or valley 24 in a ring 12, and the opposite end of arm 18g and 20g is coupled to one end of a brace element 16g. The two brace elements 16g are separated from one another, and coupled to the third arm 19g. A bridge couples every peak and valley in adjacent rings. The three arms are formed from a linear strut. The length of the brace element is preferably longer than the length of the arms in the bridge, and the width of the brace element is also preferably wider than the width of the linear struts which form the arms. The leading and trailing edges 40 (proximal and distal ends) of each brace element are tapered to smooth out sharp corners and edges. In this embodiment, the edges are beveled. In alternative embodiments, a radius may be used to smooth the leading edges of the parallelogram shaped brace. Each brace element also has an upper and lower engagement surface 36g, 34g that engages an adjacent engagement surface. In this embodiment, the engagement surfaces are flat and planar, but they may take any of the forms described herein. Other aspects of the stent 10g generally take the same form as those of the other stents described herein.

Figure 10:
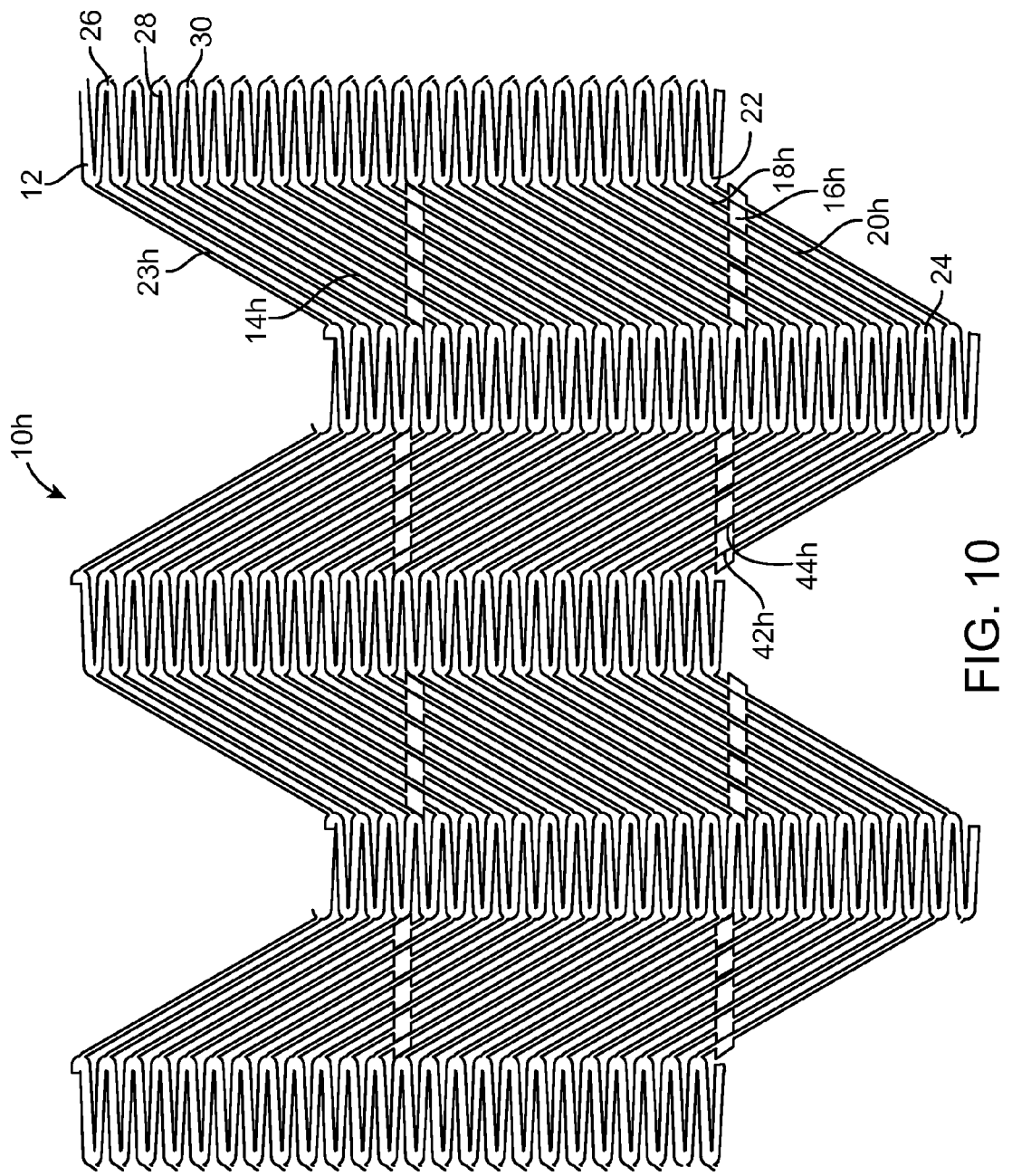
FIG. 10 illustrates yet another exemplary embodiment of a stent having brace elements that are aligned.

FIG. 10 illustrates still another exemplary embodiment of a brace stent. Stent 10h is similar to previous stents described above, with the major difference being that the brace elements on bridges are aligned to form aligned rows of brace elements between adjacent rings.

Stent 10h includes a bridge 14h between adjacent rings 12. A bridge 14h is coupled to each peak 22 and each valley 24 in adjacent rings. However, not every bridge 14h includes a brace element 16h. Thus some bridges 14h comprise only a linear strut 23h, while other bridges 14h include a brace element 16h coupled to, and disposed between adjacent arms 18h, 20h. Arms 18h, 20h are coupled to an adjacent peak or valley 22, 24. Additionally, in this embodiment, the brace elements are arranged on the bridges such that they are circumferentially aligned with one another to form an aligned row of axially oriented brace elements between adjacent rings. This embodiment has two rows of brace elements between adjacent rings. Because of the alignment of the brace elements, the engagement surfaces of the brace elements are now proximal and distal lateral engagement surfaces 44h, 42h, unlike other embodiments where the engagement surfaces are upper and lower surfaces of the brace element. Additionally, due to the use of brace elements only on selected bridges, the lateral engagement surfaces 44h, 42h engage an adjacent linear strut 23h when the stent 10h is collapsed during loading, or when an axially oriented force is applied to the stent during deployment. Other aspects of the stent 10h generally take the same form as stents previously described above. The lengths of the arms 18h, 20h vary along different bridges due to the alignment of the brace elements. However, in general, the length of one set of arms (e.g. 20h) will shorten while the length of the other set of arms (e.g. 18h) will lengthen.

As discussed above, the stents described herein may be balloon expandable, self-expanding, or a combination thereof. Preferably, the stents are self-expanding, and they are preferably formed from superelastic material. In one specific aspect, the superelastic material is Nitinol, an intermetallic compound having approximately 50.8 atomic percent Nickel and the balance Titanium. Nitinol has the unique properties of shape memory and superelasticity, and in this application is designed to take advantage of the material's ability to withstand unusually high levels of strain (up to 8% or more), without experiencing plastic deformation. The material can have an unusually pronounced hysteresis effect in its stress-strain relationship: when subjected to loading, stresses are relatively high, as they reach the upper plateau (UP) where a phase change from austenite to martensite occurs. When the material is unloaded, stresses are relatively low, as seen in the lower plateau (LP) where the material transforms from martensite to austenite. The magnitude of the difference between UP and LP stresses is determined by material composition, as well as thermal and processing history. In this application, the transition temperature for the material, known as the Austenite Finish ($A_f$) temperature is preferably set between 10 degrees and 40 degrees, and more preferably set to between 10 degrees and 37 degrees C. Preferentially, the $A_f$ temperature is set close to body temperature to maximize the hysteresis effect of the material, increasing the difference between UP and LP. As such, forces exerted by the stent as it unloads (expands) from its constrained state are minimized: this force, described as Chronic Outward Force (COF), is controlled by the LP stress. Conversely, the forces exerted by the stent when it is loaded (subjected to external compression) are maximized: this force, described as Radial Resistive Force (RRF), is controlled by the UP stress.

Any of the stent embodiment disclosed herein may also be used to deliver a therapeutic agent from the stent to tissue. Exemplary therapeutic agents include anti-restenosis agents such as paclitaxel, rapamycin and analogs thereof such as everolimus, biolimus A9, etc., or other anti-stenosis agents known to those of skill in the art. Other therapeutic agents may include anti-thrombogenics/anti-thrombolytics such as heparin, tissue plaminogen activator (tPA), as well as other therapeutic agents such as antibiotics, etc. One of skill in the art appreciates that these agents may be coated, layered, or otherwise applied to the stent using known methods so that the agent may be controllably eluted therefrom.

Figure 11A:
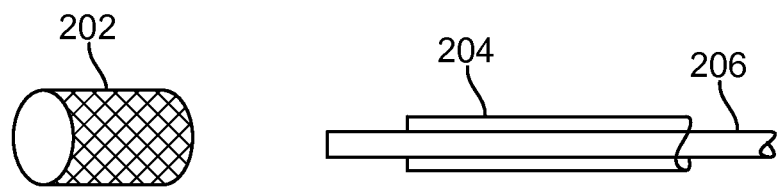
FIGS. 11A-11C illustrate an exemplary method of loading a stent onto a delivery catheter.
Figure 11B:
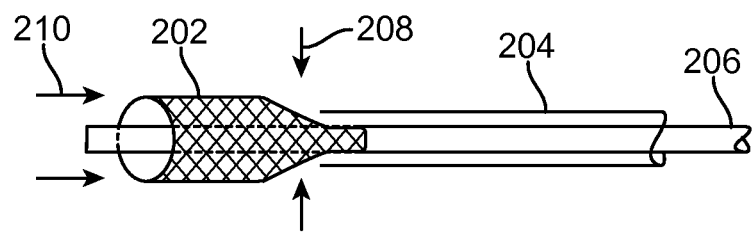
Figure 11C:
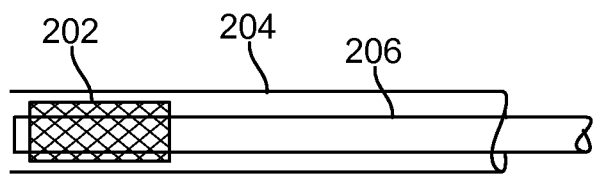

FIGS. 11A-11C illustrate an exemplary method of loading any of the stent embodiments disclosed herein onto a delivery catheter. In FIG. 11A, stent 202 is in its unbiased, radially expanded configuration. The delivery system includes a central shaft 206 having an outer constraining sheath 204 slidably disposed thereover. A radially inward force 208 is applied to stent 202 in FIG. 11B, and an axially oriented force 210 is used to simultaneously push and compress stent 202 over inner shaft 206, and under sheath 204. This process is continued until the stent is 202 is constrained from expansion by sheath 204, as seen in FIG. 11C. It is during this loading process that the brace elements of the stent (not shown) engage one another and prevent the stent from unwanted deformation such as buckling. Once loaded onto the delivery catheter, the stent may be delivered to a desired treatment site.

The stents disclosed herein may be used to treat any number of diseases. In an exemplary method of usage, the physician will gain intraluminal access to the target location of the anatomy using standard techniques (e.g. percutaneous techniques such as the Seldinger technique, or cutdown methods), and may perform diagnostic imaging to help identify the location and extent for the need of stenting. Diagnostic imaging may include x-ray or fluoroscopy, endoscopy, magnetic resonance, ultrasound, intravascular ultrasound (IVUS), and computed tomography.

In the preferred method of use, the delivery system is used to treat vascular disease, specifically venous disease (i.e. iliac vein compression syndrome, post-thrombotic syndrome) to improve venous outflow. In a preferred embodiment, the device is hand-held by the user. The user inserts the device in the pelvic venous region using standard intravascular techniques. The stent is constrained within a flexible inner and outer sheath, preferably such that the outer sheath is compatible with an introducer sheath having a profile of 10 French or less. Typically, the physician will have already placed a 0.035" guidewire across the site of the target vessel during balloon venography prior to stenting. The physician then advances the stent delivery system over such a guidewire to the target site, and positions the stent in the desired location using x-ray and/or ultrasound guidance. After the stent has initially expanded and been anchored in the vessel, it may be advantageous to confirm accurate placement with the use of imaging (IVUS, or x-ray guidance). If the placement of the stent is not optimal, the physician may re-advance the constraining outer sheath to recapture the deployed segment of stent, reposition the delivery system, and attempt the deployment again. After the stent has been confirmed to be anchored in the intended location, the outer sheath is fully retracted, releasing the entire stent from the delivery system. The fully expanded stent is now in its final position within the iliac or femoral vein.

As a final step, it may be advantageous to inflate a balloon within the stent, particularly in the region of the obstructive lesions. With this method, the stent's outward resistive forces are maximized to ensure maximum luminal gain and relief from the symptoms associated with vascular disease. This post-dilation also helps to ensure that the expanded stent is fully tacked into position and into engagement with the vessel wall or other target tissue. Other aspects of exemplary stent delivery methods and exemplary delivery systems are disclosed in copending U.S. patent application Ser. No. 12/903,056 filed Oct. 12, 2010, and Ser. No. 12/911,604 filed Oct. 25, 2010, the entire contents of each is incorporated herein by reference.

It would also be desirable to provide an intravascular ultrasound (IVUS) catheter that is designed to work in conjunction with the stent and delivery system described herein. Preferentially, the IVUS probe would be contained within the profile of a standard 0.035" guidewire, and could therefore be used to replace the conventional guidewire for balloon and stent delivery while providing opportunity for imaging throughout the procedure.

Figure 12A:
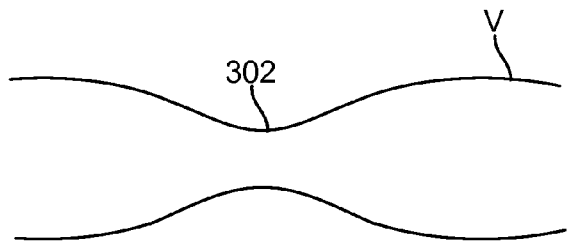
FIGS. 12A-12E illustrate an exemplary method of deploying a stent.
Figure 12B:
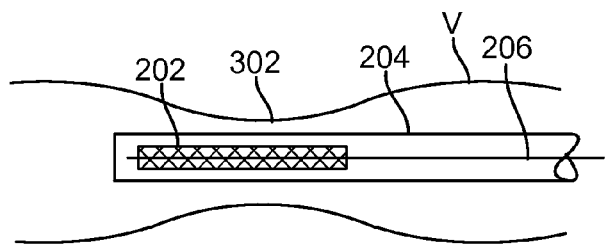
Figure 12C:
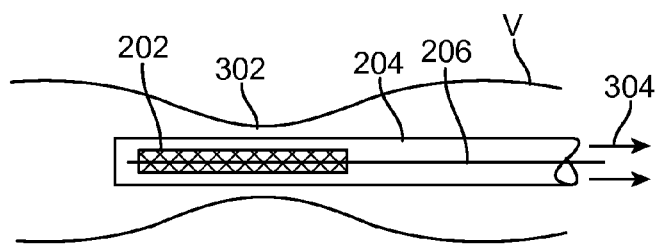
Figure 12D:
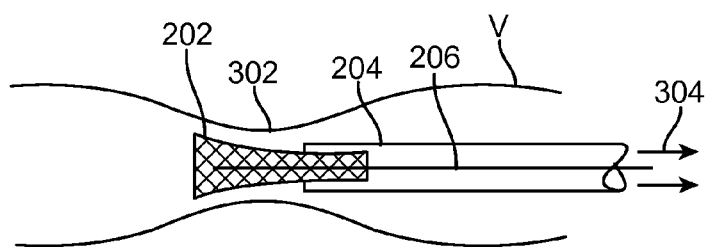
Figure 12E:
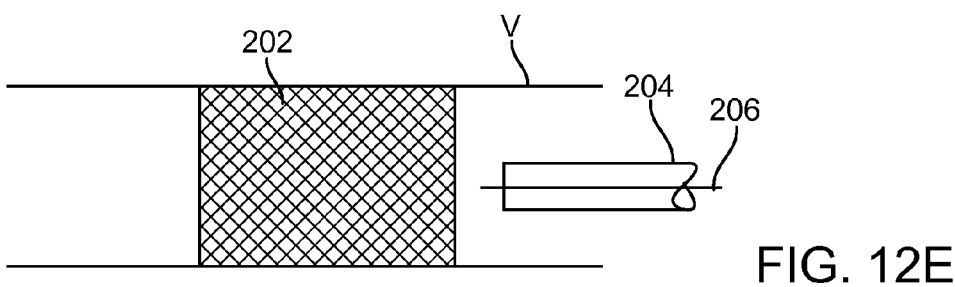

FIGS. 12A-12E illustrate the basic steps of stent deployment in an exemplary embodiment used to treat venous compression syndrome. FIG. 12A illustrates the target treatment region of a vein V that is compressed 302 due to externally applied forces from an adjacent vessel, ligament, tumor, or other tissue. The delivery catheter which comprises a central elongate shaft 206, outer constraining sheath 204 and stent 202 are percutaneously introduced into the vessel and transluminally advanced to the treatment site as seen in FIG. 12B. The outer sheath 204 is proximally retracted 304 as illustrated in FIG. 12C and then stent 202 begins to self-expand as shown in FIG. 12D. During sheath retraction, friction between the stent and sheath may result in axially oriented forces which can cause the stent to deform or buckle in an undesired fashion. However, the axially oriented forces may also cause the brace elements of the stent to engage one another, thereby providing additional support and rigidity to the stent, thereby preventing unwanted deformation. The outer sheath is fully refracted until stent 202 is fully expanded into engagement with the vessel, alleviating the compression 302 caused by the external forces. The delivery catheter may then be retracted and removed from the patient.

Although the exemplary embodiments have been described in some detail for clarity of understanding and by way of example, a variety of additional modifications, adaptations and changes may be clear to those of skill in the art. One of skill in the art will appreciate that the various features described herein may be combined with one another or substituted with one another. Hence, the scope of the present invention is limited solely by the appended claims.

What is claimed is:

1. A stent comprising:
   a plurality of radially expandable rings each having a contracted configuration suitable for delivery and a radially expanded configuration for engaging and supporting tissue,
   wherein each ring is formed from a plurality of interconnected struts, adjacent struts in each ring being connected together with a connector, and each ring having a proximal end, and a distal end, wherein the plurality of rings are coaxially aligned with one another to form a longitudinal axis, wherein a distal end of one ring faces a proximal end of an adjacent ring; and
   a plurality of bridges disposed between adjacent rings, the plurality of bridges coupling adjacent rings together, wherein one or more of the bridges comprise a first end, a second end, and a first brace element therebetween, wherein the first end of the bridge is coupled with the distal end of a first ring at a first connection point, and the second end of the bridge is coupled with the proximal end of an adjacent second ring at a second connection point,
   wherein the first brace element of one bridge and a second brace element of an adjacent bridge each comprise an upper engagement surface and a lower engagement surface, the upper and lower engagement surfaces of the first brace element extending from a proximal end to a distal end of the first brace element, the upper and lower engagement surfaces of the second brace element extending from a proximal end to a distal end of the second brace element, wherein substantially an entirety of the upper engagement surface of the first brace element engages substantially an entirety of the lower engagement surface of the second brace element of the adjacent bridge when the corresponding adjacent rings are in the contracted confinguration, and
   wherein the one or more bridges comprise a first arm and a second arm, with the first brace element disposed therebetween, a length of the first arm or the second arm is greater than a length of the first brace element and the first brace element is wider than the first arm or the second arm.

2. The stent of claim 1, wherein the plurality of interconnected struts form a series of peaks and valleys.

3. The stent of claim 2, wherein the peaks and valleys of a first ring are in phase with the peaks and valleys of an adjacent ring.

4. The stent of claim 2, wherein the connector interconnecting the plurality of struts is U-shaped or V-shaped.

5. The stent of claim 1, wherein the rings are self-expanding.

6. The stent of claim 1, wherein the rings are balloon expandable.

7. The stent of claim 1, wherein the first connection point is circumferentially offset relative to the second connection point so that the bridge is transverse to the longitudinal axis.

8. The stent of claim 1, wherein the first arm or the second arm comprises a linear strut.

9. The stent of claim 2, wherein the first connection point is on a peak of one ring, and the second connection point is on a valley of an adjacent ring.

10. The stent of claim 9, wherein the first connection point is on the apex of the peak.

11. The stent of claim 9, wherein the second connection point is on the bottom of the valley.

12. The stent of claim 1, wherein a bridge element couples each pair of adjacent struts interconnected together in a first ring with a pair of adjacent struts interconnected together in an adjacent second ring or an adjacent third ring.

13. The stent of claim 1, wherein the first brace element comprises a parallelogram shaped region.

14. The stent of claim 1, wherein the upper engagement surfaces and the lower engagement surfaces comprise planar surfaces.

15. The stent of claim 1, wherein the upper engagement surface of the first brace element has a first contour and the lower engagement surface of the second brace element on the adjacent brace has a second contour, the first contour nesting with the second contour.

16. The stent of claim 1, wherein the one or more bridges comprise a plurality of brace elements, the bridges joining the two adjacent rings together, and wherein the brace elements on each bridge are axially aligned with one another to form a circumferentially oriented column of braces.

17. The stent of claim 1, wherein the one or more bridges comprise a plurality of brace elements, the bridges joining the two adjacent rings together, and wherein the brace elements on each bridge are circumferentially aligned with one another to form an axially oriented row of braces.

18. The stent of claim 1, wherein the one or more bridges comprise a plurality of brace elements, the bridges joining the two adjacent rings together, and wherein a brace on a first bridge is axially offset relative to a brace on the adjacent ring.

19. The stent of claim 1, wherein the one or more bridges comprise a plurality of brace elements, the bridges joining the two adjacent rings together, and wherein the braces form a circumferentially staggered pattern.

20. The stent of claim 1, wherein a first bridge couples a first ring and a second adjacent ring, and a second bridge couples the second ring with a third ring adjacent the second ring, and wherein the first bridge has a first slope, and the second bridge has a second slope opposite the first bridge.

21. The stent of claim 1, wherein the first brace element does not contact a brace element of an adjacent bridge when the corresponding rings are in the radially expanded configuration.

22. The stent of claim 1, wherein the plurality of bridges disposed between adjacent rings comprise a plurality of bridges substantially parallel with one another.

23. The stent of claim 1, wherein the one or more bridges comprises a length, and the first brace element comprises a length shorter than the bridge length.

24. The stent of claim 1, wherein the one or more bridges comprises a second brace element separated from the first bridge by a strut.

25. The stent of claim 1, wherein the one or more bridges comprises a plurality of brace elements.

26. The stent of claim 24, wherein the one or more bridges comprises a plurality of bridges each having a first brace and a second brace separated by a strut, the plurality of bridges joining two adjacent rings together, and wherein the first brace elements on each bridge are circumferentially aligned with one another, and the second brace elements on each bridge are circumferentially aligned with one another, thereby forming a first column of circumferentially oriented brace elements and a second column of circumferentially oriented brace elements.

27. The stent of claim 1, wherein first brace element comprises a slotted region extending through the entire thickness of the brace element.

28. The stent of claim 1, wherein the first brace element comprises a solid tab without slots extending therethrough.

29. The stent of claim 1, wherein a pair of bridges each having a brace element and joining two adjacent rings are separated by a bridge without a brace element and joining the two adjacent rings.

30. The stent of claim 1, wherein at least some of the plurality of interconnected struts remain unconnected with a bridge.

31. The stent of claim 1, wherein at least some of the bridges comprise a brace element having a tapered proximal or distal end.

32. The stent of claim 1, wherein the first and second arms are co-linear with the first brace element.

* * * * *